March 25, 1947. M. DENOYEL Plant Pat. 725
ROSE PLANT
Filed Oct. 26, 1943
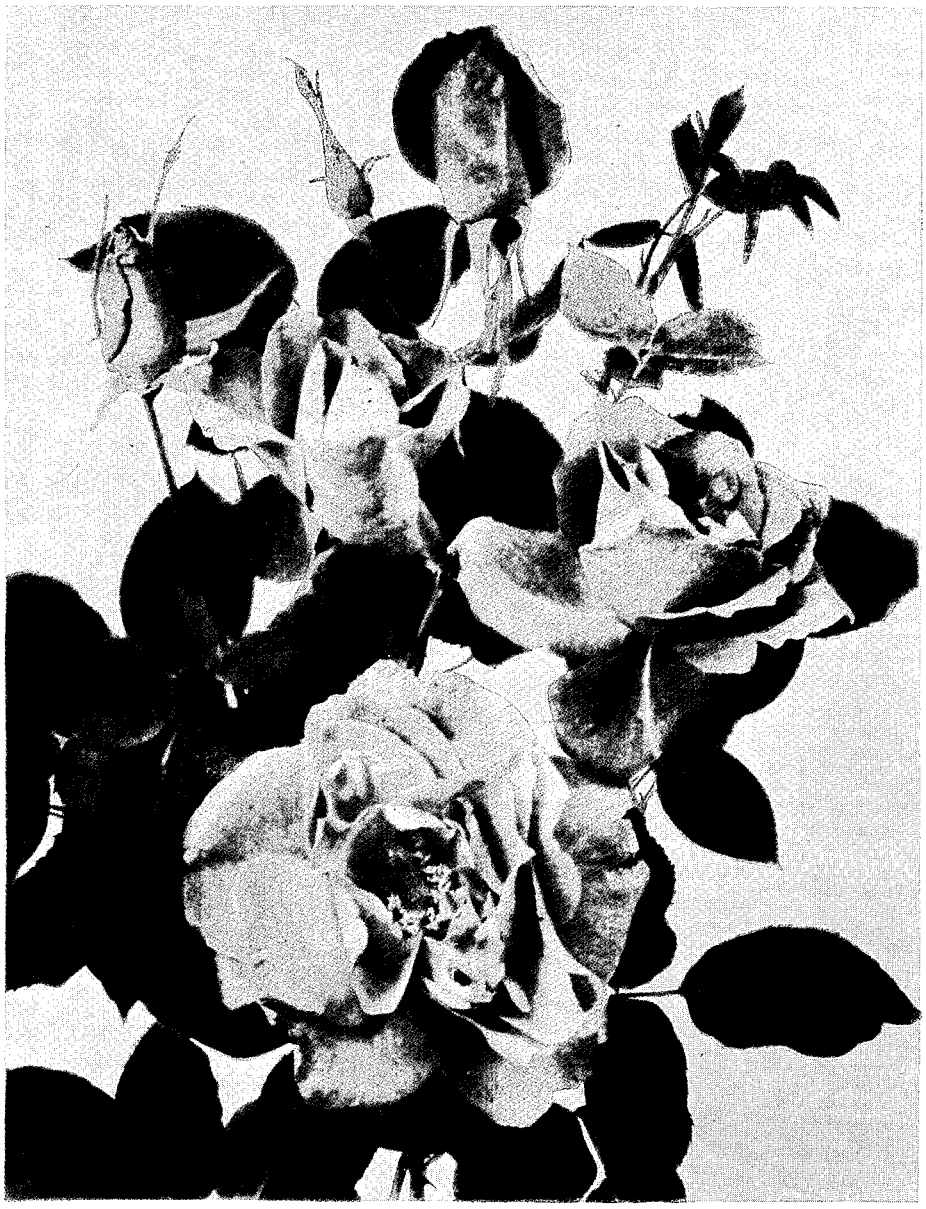
Inventor
Marguerite Denoyel
By Robb & Robb
Attorneys Patented Mar. 25, 1947

UNITED STATES PATENT OFFICE

725

ROSE PLANT

Marguerite Denoyel, Venissieux, near Lyon, France, assignor to Jackson & Perkins Company, Newark, N. Y., a corporation of New York Application October 26, 1943, Serial No. 507,719

1 Claim. (Cl. 47—61)

The present invention relates to a new and distinct variety of hybrid tea rose plant, particularly appealing to rosarians because of its exceptionally large, graceful flowers of vivid flashing rose red color borne by medium length stem in groups of several to the stem, and its consequential value as a decorative plant.

The flowers of this new rose, as clearly shown in the accompanying illustration, are further characterized by their open center when full blown, presenting an attractive contrast of color, especially enhanced by the setting of yellow-green young foliage.

The imbricated form of the petals and the long sepals which unfold in a decorative manner add materially to the attractiveness of this new rose.

Asexual reproduction shows that these characteristics hold true through succeeding propagations.

The following is a detailed description of this new variety, color terminology being in accord with Ridgway's Color Standard:

Parentage: Seedling—Parents unknown.
Classification: Botanical and commercial—hybrid tea.

*Flower*

(Observations made in the nurseries of Jackson & Perkins Company, Newark, New York, in the afternoon of October 10, 1943.)

Blooming Habit: Recurrent—continuous.
Bud:
- *Size.*—Large.
- *Form.*—Pointed. Is not affected by wet or hot weather.
- *Color.*—When sepals first divide—Carmine, Plate 1; when petals begin to unfurl—Pomegranate Purple, Plate 12, lightly overcast with Rose Red, Plate 12; when half blown—inside of petals, Rose Red, Plate 12, faintly overcast with Pomegranate Purple, Plate 12; reverse of petals, Tyrian Rose, Plate 12.
- *Sepals.*—Branched, "hood" above bud; curl back when petals begin to unfurl. *Color.*—inside—Veronese Green, Plate 18; outside—Parrot Green, Plate 16.
- Calyx.—Shape—pear. Size—small. Aspect—smooth. Color—Light Cress Green, Plate 31. Odor when rubbed—none.
- *Peduncle.*—Length—medium. Aspect—rough. Color—Yellowish Oil Green, Plate 5. Strength—bending; slender.
- *Opening.*—Opens up well; is not affected by adverse conditions.

Bloom:

- *Size.*—Very large. Average size when fully expanded, 5½–6 inches.
- *Borne.*—Several together.
- *Stems.*—Medium length; normal strength.
- *Form.*—When first open, cupped. *Permanence.*—flattens.
- *Petalage.*—Double (full but open center). Number of petals under normal conditions, 20 to 25.
- *Colors.*—Center of flower—Rose Red, Plate 12. Outer petals—Rose Red, Plate 12, lightened by Tyrian Rose, Plate 12. Base of petals (aiglet)—Lemon Chrome, Plate 4. Inside of petals—Rose Red, Plate 12, overcast with Tyrian Rose, Plate 12. Reverse of petals—Rose Red, Plate 12, overcast with Rose Color, Plate 12. General tonality from a distance—Rose Red, Plate 12.
- *Discoloration.*—General tonality at end of first day—Rose Red, Plate 12, lightened with Tyrian Rose, Plate 12. Second day—Rose Red, Plate 12, lightened with Tyrian Rose, Plate 12. Third day—Tyrian Rose, Plate 12.

Petals:
- *Texture.*—Leathery; is not affected by wet or hot weather.
- *Appearance.* — Inside — velvety; outside—shiny.
- *Form.*—Round, scalloped.
- *Arrangement.*—Imbricated (regularly arranged shingle-like). Petaloids in center—none.
- *Persistence.*—Drop off cleanly.
- *Fragrance.*—Strong. Nature — heavy "Old Rose perfume."
- *Lasting quality.*—On the plant and as cut flower—long.

Genital organs:
- *Stamens, anthers.*—Large; many. Color—Orange Buff, Plate 3. Arrangement—regular around styles.
- *Stamens, filaments (threads).* — Medium length. Color—Jasper Red, Plate 13.
- *Pollen.*—Pale Yellow-Orange, Plate 3.
- *Styles.*—Bunched, uneven length; medium length; thin.
- *Stigmas.*—Maize Yellow, Plate 4.
- *Ovaries.*—All enclosed in calyx.

*Plant*

Form: Bush.
Growth: Vigorous; branching.
Foliage: 3 to 5 leaflets.
- *Size.*—Large.
- *Quantity.*—Abundant.

3

*Color.*—New foliage: upper side—Yellowish Oil Green, Plate 5, with serrations Van Dyke Red, Plate 13; under side—Biscay Green, Plate 17, overlaid with Cress Green, Plate 31. Old foliage: upper side—Dark Cress Green, Plate 31; under side—Light Cress Green, Plate 31.

*Shape.*—Oval pointed.

*Texture.*—Upper side—leathery; under side—smooth. Ribs and veins—ordinary.

*Edge.*—Serrated (saw toothed).

*Serration.*—Single; small.

*Rachis.*—Rainette Green, Plate 31. Under side—prickles.

*Stipules.*—Long; smooth.

*Disease resistance.*—Resistant, as indicated by the fact that plants of this variety have been grown in test gardens where they are exposed to the normal ills of such environment and failed to acquire any of the common diseases.

Wood:

4

*New Wood.*—Color—Yellowish Oil Green, Plate 5. Bark—smooth.

*Old Wood.*—Color—Light Hellebore Green. Plate 17. Bark—smooth.

Thorns (thorns are divided into thorns, prickles, and short needles);

*Thorns.*—On main stalks from base—few; on laterals from stalk—none. Form—narrow base; short; hooked downward. Color when young—Acajou Red, Plate 13. Position—irregular.

*Prickles.*—None.

*Short needles.*—None.

I claim:

A new and distinct variety of rose plant, characterized as to novelty by the exceptionally large flowers of vivid rose red color and open center when full blown, the imbricated form of petals and long sepals, and the yellow-green young foliage, substantially as shown and described.

MARGUERITE DENOYEL.